Figure 1:
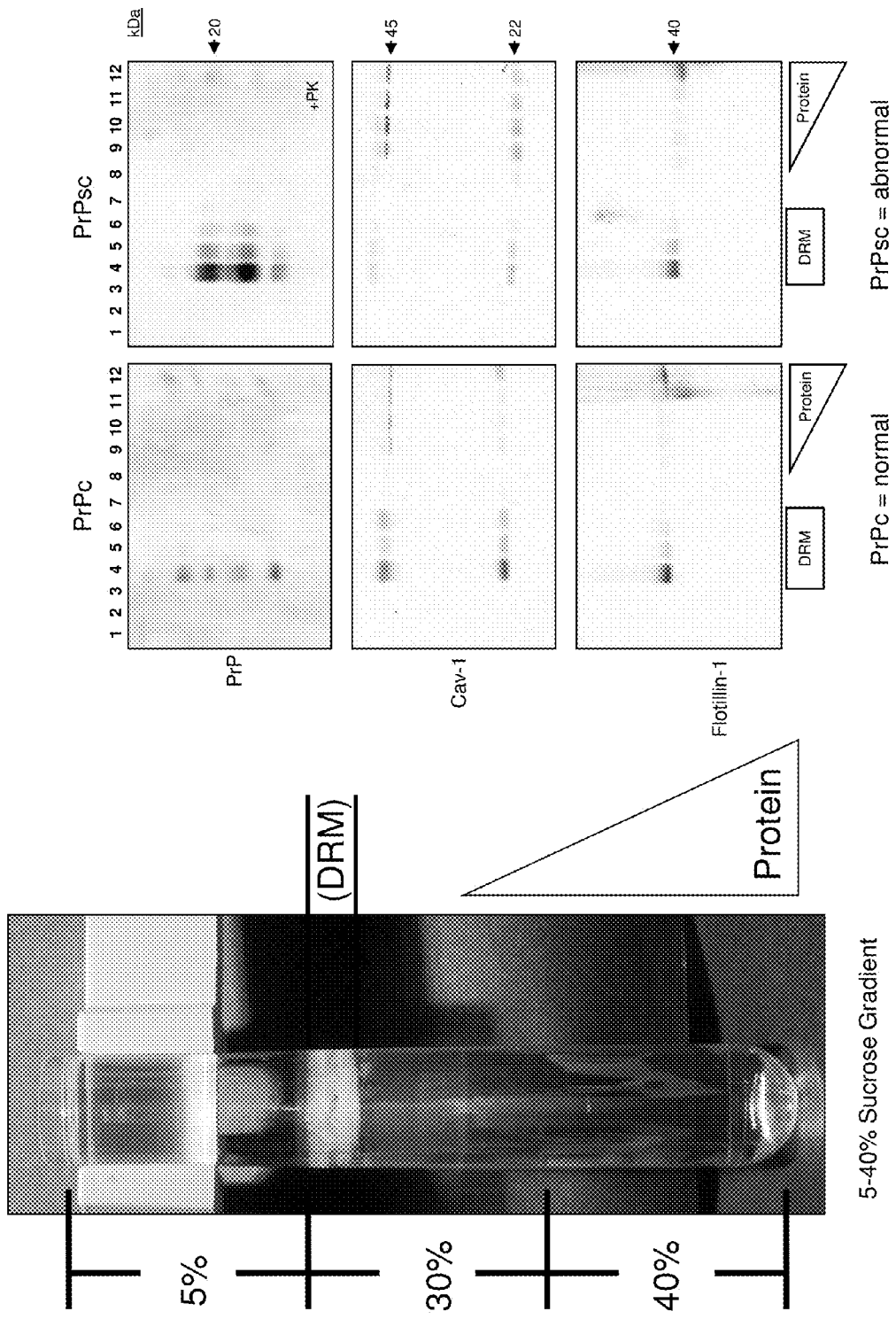
Figure 3:
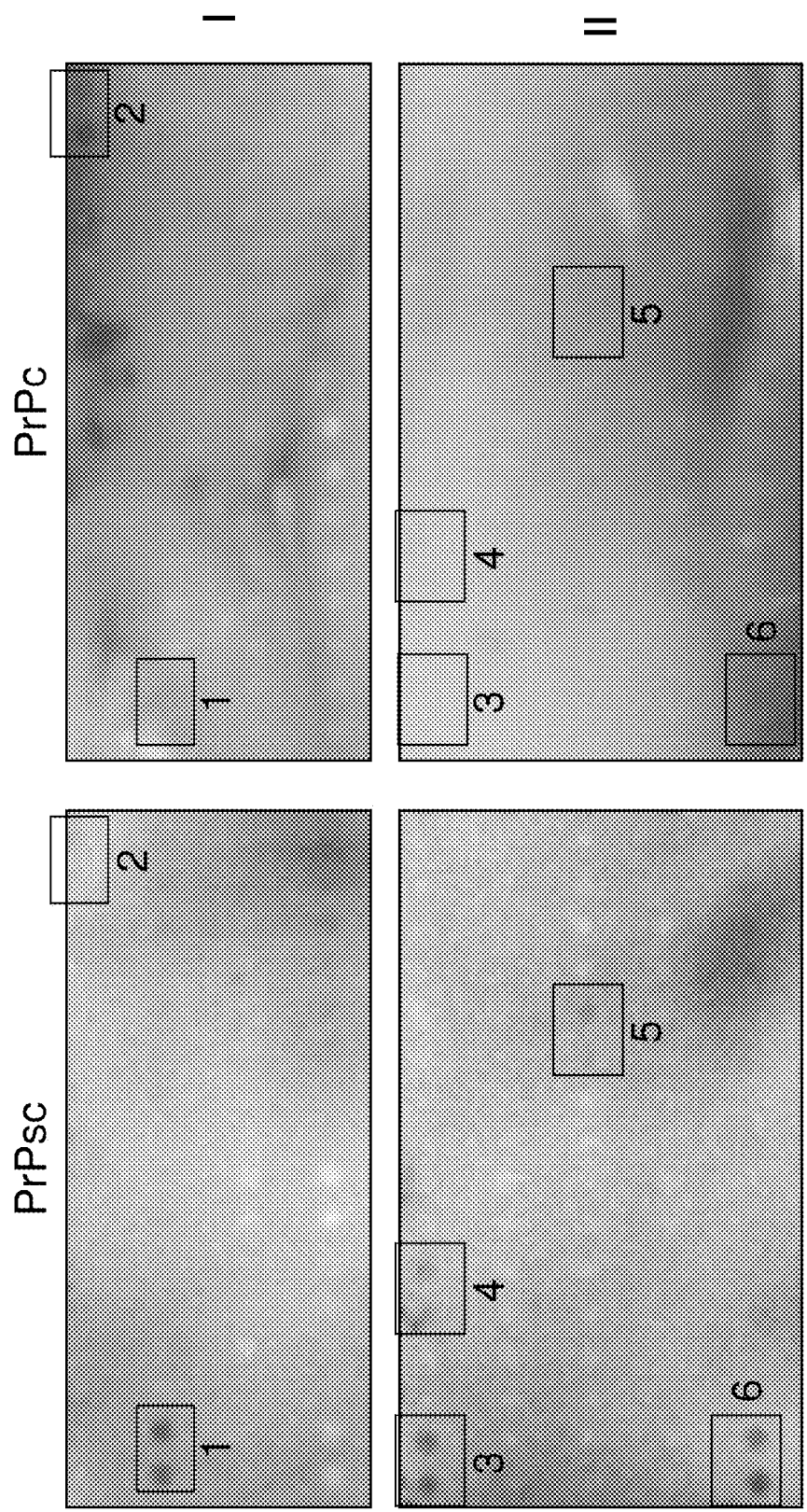
Figure 4:
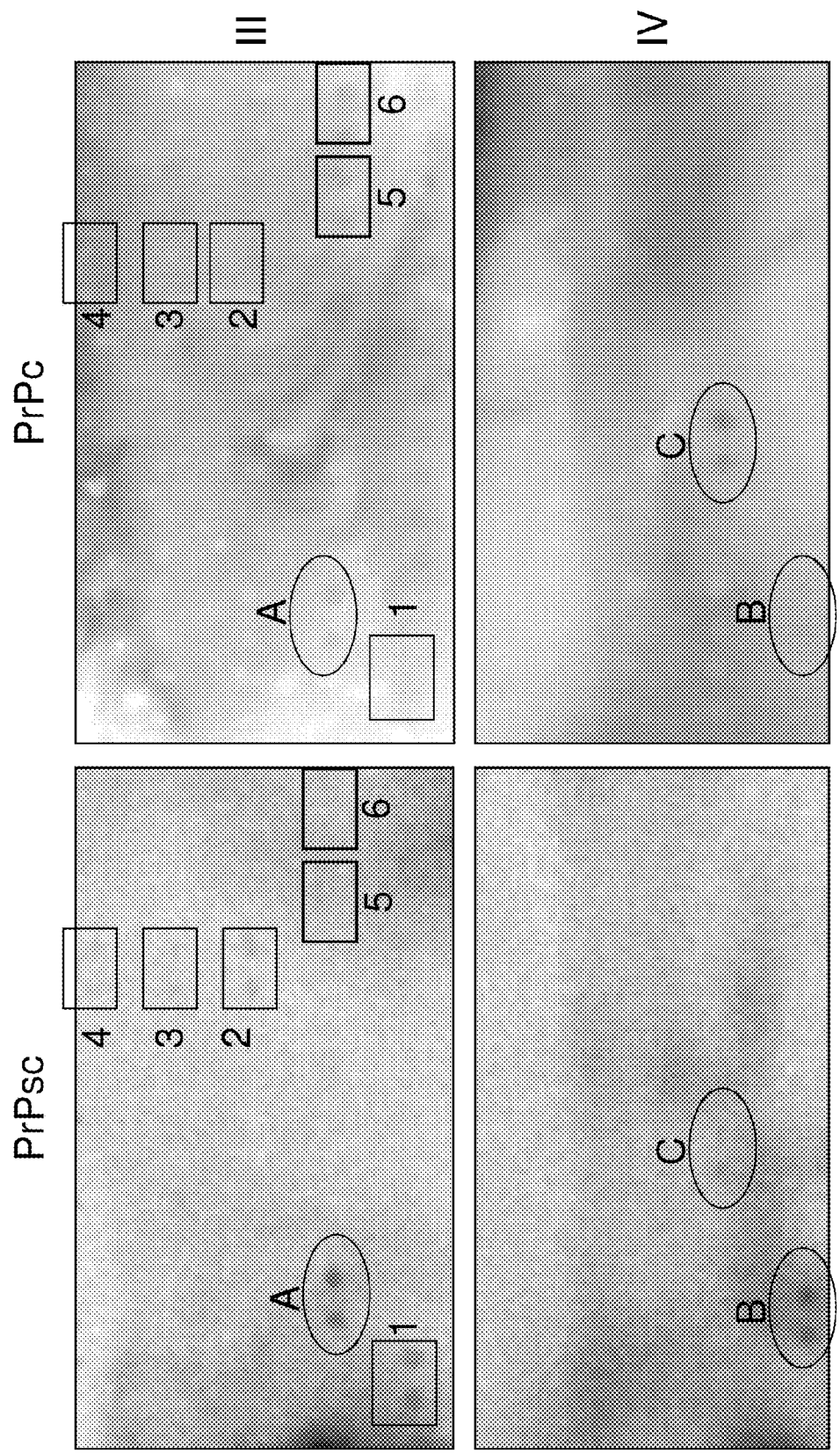
Figure 5:
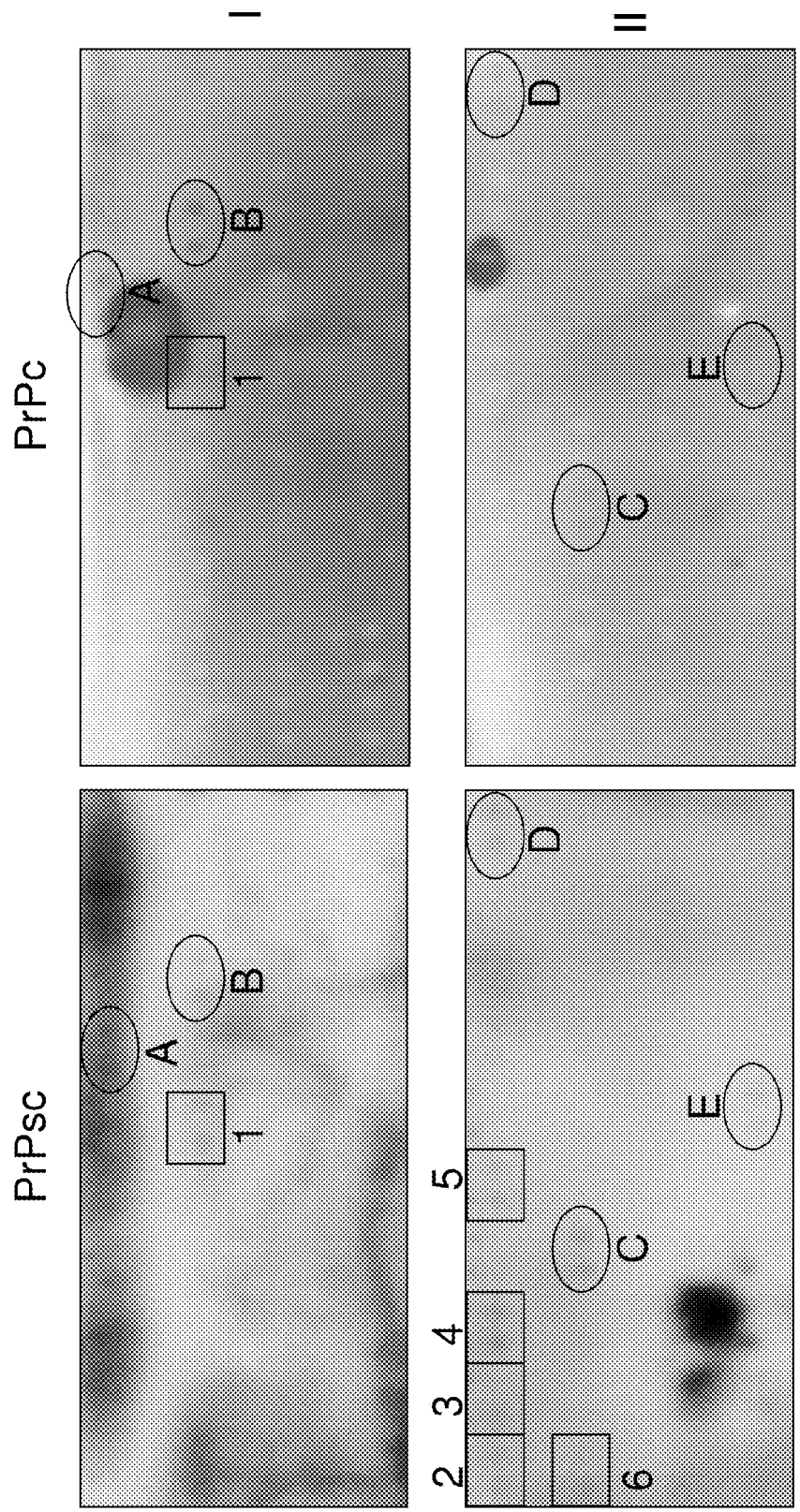
Figure 6:
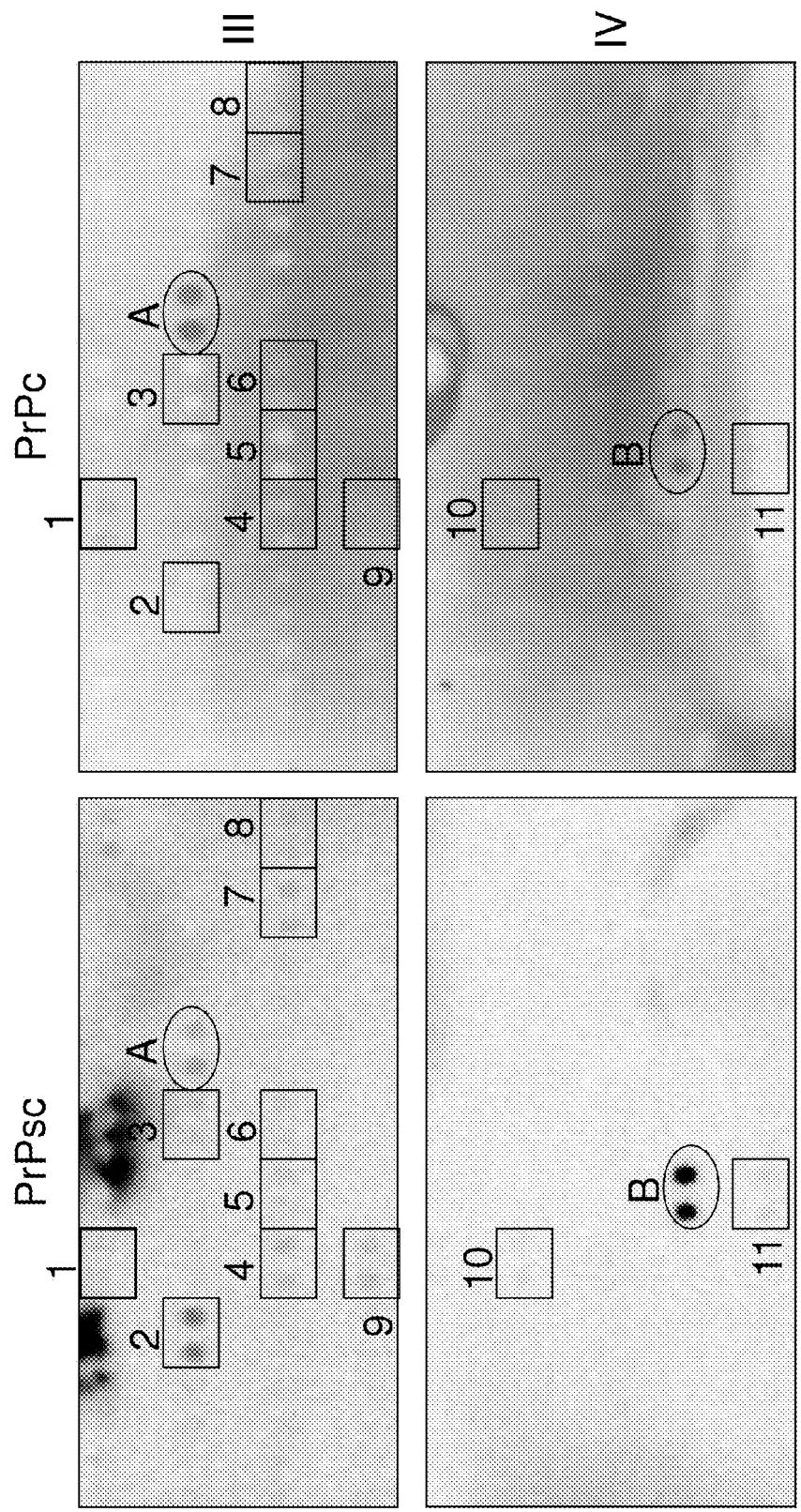
Figure 7:
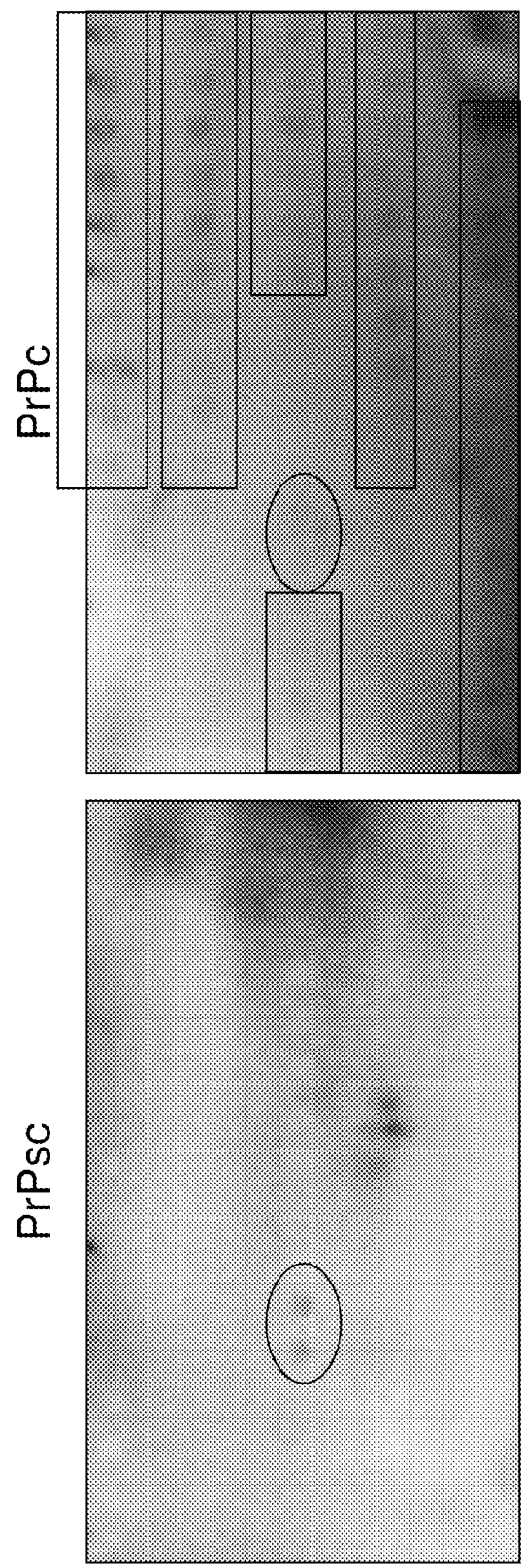
Figure 8:
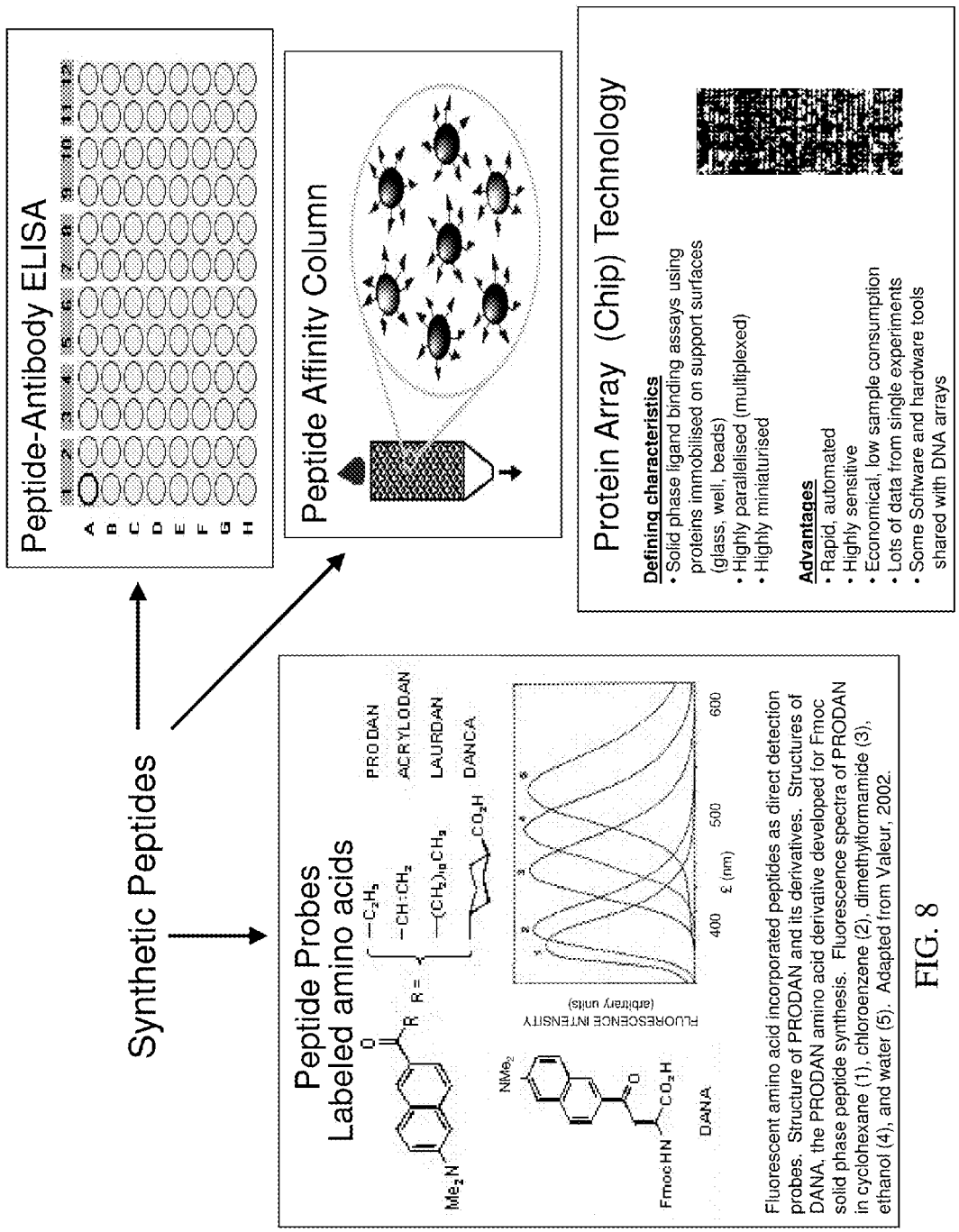

US008541166B1

(12) United States Patent
Hnasko et al.

(10) Patent No.: US 8,541,166 B1
(45) Date of Patent: Sep. 24, 2013

(54) PEPTIDE SEQUENCES FOR BINDING INFECTIOUS PRIONS

(75) Inventors: Robert M. Hnasko, Port Costa, CA (US); Cathrin E. Bruederle, Portland, OR (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 977 days.

(21) Appl. No.: 12/571,275

(22) Filed: Sep. 30, 2009

Related U.S. Application Data

(60) Provisional application No. 61/101,447, filed on Sep. 30, 2008.

(51) Int. Cl.

| | |
|---|---|
| *C12Q 1/00* | (2006.01) |
| *G01N 33/53* | (2006.01) |
| *G01N 33/569* | (2006.01) |

(52) U.S. Cl.
USPC .................................. 435/4; 435/7.1; 435/7.2

(58) Field of Classification Search
None
See application file for complete search history.

(56) References Cited

U.S. PATENT DOCUMENTS 7,312,041 B2 * 12/2007 Lu et al. ......................... 435/7.1

* cited by examiner

*Primary Examiner* — Jeffrey Stucker
*Assistant Examiner* — Stephen Gucker
(74) *Attorney, Agent, or Firm* — Howard V. Owens, Jr.; Lesley Shaw; John D. Fado

(57) ABSTRACT

Peptide sequences that specifically bind infectious prion protein for the generation of antibodies and therapeutic agents are disclosed herein.

1 Claim, 8 Drawing Sheets

PrPc

PrPsc

1 = WW domain peptide (sequence confirmed)

FIG. 2

SEQUENCE LISTING

```
<160> NUMBER OF SEQ ID NOS: 25

<210> SEQ ID NO 1
<211> LENGTH: 92
<212> TYPE: PRT
<213> ORGANISM: Artificial Sequence
<220> FEATURE:
<223> OTHER INFORMATION: PDZ 2750 - 2835 aa

<400> SEQUENCE: 1

Val His Asp Ala Leu Cys Val Glu Val Leu Lys Thr Ser Ala Gly Leu
1               5                   10                  15

Gly Leu Ser Leu Asp Gly Gly Lys Ser Ser Val Thr Gly Asp Gly Pro
            20                  25                  30

Leu Val Ile Lys Arg Val Tyr Lys Gly Gly Ala Ala Glu Gln Ala Gly
        35                  40                  45

Ile Ile Glu Ala Gly Asp Glu Ile Leu Ala Ile Asn Gly Lys Pro Leu
    50                  55                  60

Val Gly Leu Met His Phe Asp Ala Trp Asn Ile Met Lys Ser Val Pro
65                  70                  75                  80

Glu Gly Pro Val Gln Leu Leu Ile Arg Lys His Arg
                85                  90

<210> SEQ ID NO 2
<211> LENGTH: 87
<212> TYPE: PRT
<213> ORGANISM: Artificial Sequence
<220> FEATURE:
<223> OTHER INFORMATION: PDZ 193 - 279 aa

<400> SEQUENCE: 2

Glu Ile Lys Leu Phe Lys Gly Pro Lys Gly Leu Gly Phe Ser Ile Ala
1               5                   10                  15

Gly Gly Val Gly Asn Gln His Ile Pro Gly Asp Asn Ser Ile Tyr Val
            20                  25                  30

Thr Lys Ile Ile Asp Gly Gly Ala Ala Gln Lys Asp Gly Arg Leu Gln
        35                  40                  45

Val Gly Asp Arg Leu Leu Met Val Asn Asn Tyr Ser Leu Glu Glu Val
    50                  55                  60

Thr His Glu Glu Ala Val Ala Ile Leu Lys Asn Thr Ser Glu Val Val
65                  70                  75                  80

Tyr Leu Lys Val Gly Asn Pro
                85
```

```
<210> SEQ ID NO 3
<211> LENGTH: 93
<212> TYPE: PRT
<213> ORGANISM: Artificial Sequence
<220> FEATURE:
<223> OTHER INFORMATION: PDZ 17 - 105 aa

<400> SEQUENCE: 3

Ser Arg Val His Glu Cys Thr Val Lys Arg Gly Pro Gln Gly Glu Leu
1               5                   10                  15

Gly Val Thr Val Leu Gly Gly Ala Glu His Gly Glu Phe Pro Tyr Val
            20                  25                  30

Gly Ala Val Ala Ala Val Glu Ala Ala Gly Leu Pro Gly Gly Gly Glu
        35                  40                  45

Gly Pro Arg Leu Gly Glu Gly Glu Leu Leu Leu Glu Val Gln Gly Val
    50                  55                  60

Arg Val Ser Gly Leu Pro Arg Tyr Asp Val Leu Gly Val Ile Asp Ser
65                  70                  75                  80

Cys Lys Glu Ala Val Thr Phe Lys Ala Val Arg Gln Gly
                85                  90

<210> SEQ ID NO 4
<211> LENGTH: 96
<212> TYPE: PRT
<213> ORGANISM: Artificial Sequence
<220> FEATURE:
<223> OTHER INFORMATION: PDZ 1147 - 1229 aa

<400> SEQUENCE: 4

Asp Phe Asp Tyr Phe Thr Val Asp Met Glu Lys Gly Ala Lys Gly Phe
1               5                   10                  15

Gly Phe Ser Ile Arg Gly Gly Arg Glu Tyr Lys Met Asp Leu Tyr Val
            20                  25                  30

Leu Arg Leu Ala Glu Asp Gly Pro Ala Ile Arg Asn Gly Arg Met Arg
        35                  40                  45

Val Gly Asp Gln Ile Ile Glu Ile Asn Gly Glu Ser Thr Arg Asp Met
    50                  55                  60

Thr His Ala Arg Ala Ile Glu Leu Ile Lys Ser Gly Gly Arg Arg Val
65                  70                  75                  80

Arg Leu Leu Leu Lys Arg Gly Thr Gly Gln Val Pro Gln Tyr Asp Glu
                85                  90                  95

<210> SEQ ID NO 5
<211> LENGTH: 100
<212> TYPE: PRT
<213> ORGANISM: Artificial Sequence
<220> FEATURE:
<223> OTHER INFORMATION: PDZ 728 - 815 aa

<400> SEQUENCE: 5

Glu Glu Glu Leu Thr Leu Thr Ile Leu Arg Gln Thr Gly Gly Leu Gly
1               5                   10                  15

Ile Ser Ile Ala Gly Gly Lys Gly Ser Thr Pro Tyr Lys Gly Asp Asp
            20                  25                  30

Glu Gly Ile Phe Ile Ser Arg Val Ser Glu Glu Gly Pro Ala Ala Arg
        35                  40                  45

Ala Gly Val Arg Val Gly Asp Lys Leu Leu Glu Val Asn Gly Val Ala
    50                  55                  60

Leu Gln Gly Ala Glu His His Glu Ala Val Glu Ala Leu Arg Gly Ala
65                  70                  75                  80
```

```
Gly Thr Ala Val Gln Met Arg Val Trp Arg Glu Arg Met Val Glu Pro
                85                  90                  95
Glu Asn Ala Val
            100

<210> SEQ ID NO 6
<211> LENGTH: 78
<212> TYPE: PRT
<213> ORGANISM: Artificial Sequence
<220> FEATURE:
<223> OTHER INFORMATION: PDZ 78 - 155 aa

<400> SEQUENCE: 6

Lys Val Glu Met Arg Arg Asp Pro Val Leu Gly Phe Gly Phe Val Ala
1               5                   10                  15
Gly Ser Glu Lys Pro Val Val Arg Ser Val Thr Pro Gly Gly Pro
            20                  25                  30
Ser Glu Gly Lys Leu Ile Pro Gly Asp Gln Ile Val Met Ile Asn Asp
        35                  40                  45
Glu Pro Val Ser Ala Ala Pro Arg Glu Arg Val Ile Asp Leu Val Arg
    50                  55                  60
Ser Cys Lys Glu Ser Ile Leu Leu Thr Val Ile Gln Pro Tyr
65                  70                  75

<210> SEQ ID NO 7
<211> LENGTH: 90
<212> TYPE: PRT
<213> ORGANISM: Artificial Sequence
<220> FEATURE:
<223> OTHER INFORMATION: PDZ 220 - 310 aa

<400> SEQUENCE: 7

Glu Leu Lys Thr Val Thr Leu Ser Lys Met Lys Gln Ser Leu Gly Ile
1               5                   10                  15
Ser Ile Ser Gly Gly Ile Glu Ser Lys Val Gln Pro Met Val Lys Ile
            20                  25                  30
Glu Lys Ile Phe Pro Gly Gly Ala Ala Phe Leu Ser Gly Ala Leu Gln
        35                  40                  45
Ala Gly Phe Arg Glu Pro Met Glu Leu Val Val Arg Val Glu Leu Val
    50                  55                  60
Ala Val Asp Gly Glu Asn Leu Glu Gln Val Thr His Gln Arg Ala Val
65                  70                  75                  80
Asp Thr Ile Arg Arg Ala Tyr Arg Asn Lys
                85                  90

<210> SEQ ID NO 8
<211> LENGTH: 56
<212> TYPE: PRT
<213> ORGANISM: Artificial Sequence
<220> FEATURE:
<223> OTHER INFORMATION: SH3 1- 56 aa

<400> SEQUENCE: 8

Met Glu Ala Val Ala Lys Phe Asp Phe Thr Ala Ser Gly Glu Asp Glu
1               5                   10                  15
Leu Ser Phe His Thr Gly Asp Val Leu Lys Ile Leu Ser Asn Gln Glu
            20                  25                  30
Glu Trp Phe Lys Ala Glu Leu Gly Ser Gln Glu Gly Tyr Val Pro Lys
        35                  40                  45
Asn Phe Ile Asp Ile Gln Phe Pro
    50                  55
```

<210> SEQ ID NO 9
<211> LENGTH: 55
<212> TYPE: PRT
<213> ORGANISM: Artificial Sequence
<220> FEATURE:
<223> OTHER INFORMATION: SH3 271 - 330 aa

<400> SEQUENCE: 9

Arg Trp Ala Arg Ala Leu Tyr Asp Phe Glu Ala Leu Glu Asp Asp Glu
1               5                   10                  15

Leu Gly Phe His Ser Gly Glu Val Val Glu Val Leu Asp Ser Ser Asn
            20                  25                  30

Pro Ser Trp Trp Thr Gly Arg Leu His Asn Lys Leu Gly Leu Phe Pro
        35                  40                  45

Ala Asn Tyr Val Ala Pro Met
        50                  55

<210> SEQ ID NO 10
<211> LENGTH: 54
<212> TYPE: PRT
<213> ORGANISM: Artificial Sequence
<220> FEATURE:
<223> OTHER INFORMATION: SH3 226 - 285 aa

<400> SEQUENCE: 10

Gly Glu Pro Tyr Val Ala Ile Lys Ala Tyr Thr Ala Val Glu Gly Asp
1               5                   10                  15

Glu Val Ser Leu Leu Glu Gly Glu Ala Val Glu Val Ile His Lys Leu
            20                  25                  30

Leu Asp Gly Trp Trp Val Ile Arg Lys Asp Asp Val Thr Gly Tyr Phe
        35                  40                  45

Pro Ser Met Tyr Leu Gln
        50

<210> SEQ ID NO 11
<211> LENGTH: 52
<212> TYPE: PRT
<213> ORGANISM: Artificial Sequence
<220> FEATURE:
<223> OTHER INFORMATION: SH3 2 - 61 aa

<400> SEQUENCE: 11

Val Ile Ala Lys Trp Asp Tyr Thr Ala Gln Gln Asp Gln Glu Leu Asp
1               5                   10                  15

Ile Lys Lys Val Asn Glu Arg Leu Trp Leu Leu Asp Asp Ser Lys Thr
            20                  25                  30

Trp Trp Arg Val Arg Asn Ala Ala Asn Arg Thr Gly Tyr Val Pro Ser
        35                  40                  45

Asn Tyr Val Glu
        50

<210> SEQ ID NO 12
<211> LENGTH: 56
<212> TYPE: PRT
<213> ORGANISM: Artificial Sequence
<220> FEATURE:
<223> OTHER INFORMATION: SH3 152 -212 aa

<400> SEQUENCE: 12

Glu Glu Tyr Ile Ala Val Gly Asp Phe Thr Ala Gln Gln Val Gly Asp
1               5                   10                  15

-continued

Leu Thr Phe Lys Lys Gly Glu Ile Leu Val Ile Glu Lys Lys Pro
            20                  25                  30

Asp Gly Trp Trp Ile Ala Lys Asp Ala Lys Gly Asn Glu Gly Leu Val
            35                  40                  45

Pro Arg Thr Tyr Leu Glu Pro Tyr
            50                  55

<210> SEQ ID NO 13
<211> LENGTH: 62
<212> TYPE: PRT
<213> ORGANISM: Artificial Sequence
<220> FEATURE:
<223> OTHER INFORMATION: SH3 604 -665 aa

<400> SEQUENCE: 13

Glu Arg Glu Gln Thr His Arg Ala Val Phe Arg Phe Ile Pro Arg His
1               5                   10                  15

Pro Asp Glu Leu Glu Leu Asp Val Asp Pro Val Leu Val Glu Ala
            20                  25                  30

Glu Glu Asp Asp Phe Trp Phe Arg Gly Phe Asn Met Arg Thr Gly Glu
            35                  40                  45

Arg Gly Val Phe Pro Ala Phe Tyr Ala His Ala Val Pro Gly
            50                  55                  60

<210> SEQ ID NO 14
<211> LENGTH: 61
<212> TYPE: PRT
<213> ORGANISM: Artificial Sequence
<220> FEATURE:
<223> OTHER INFORMATION: SH3 107 -167 aa

<400> SEQUENCE: 14

Ser Asp Pro Asn Leu Phe Val Ala Leu Tyr Asp Phe Val Ala Ser Gly
1               5                   10                  15

Asp Asn Thr Leu Ser Ile Thr Lys Gly Glu Lys Leu Arg Val Leu Gly
            20                  25                  30

Tyr Asn Gln Asn Gly Glu Trp Ser Glu Val Arg Ser Lys Asn Gly Gln
            35                  40                  45

Gly Trp Val Pro Ser Asn Tyr Ile Thr Pro Val Asn Ser
            50                  55                  60

<210> SEQ ID NO 15
<211> LENGTH: 61
<212> TYPE: PRT
<213> ORGANISM: Artificial Sequence
<220> FEATURE:
<223> OTHER INFORMATION: SH3 123 -183 aa

<400> SEQUENCE: 15

Asp Asn Leu Glu Tyr Val Arg Thr Leu Tyr Asp Phe Pro Gly Asn Asp
1               5                   10                  15

Ala Glu Asp Leu Pro Phe Lys Lys Gly Glu Ile Leu Val Ile Ile Glu
            20                  25                  30

Lys Pro Glu Glu Gln Trp Trp Ser Ala Arg Asn Lys Asp Gly Arg Val
            35                  40                  45

Gly Met Ile Pro Val Pro Tyr Val Glu Lys Leu Val Arg
            50                  55                  60

<210> SEQ ID NO 16
<211> LENGTH: 60
<212> TYPE: PRT
<213> ORGANISM: Artificial Sequence

```
<220> FEATURE:
<223> OTHER INFORMATION: SH3 290 - 349 aa

<400> SEQUENCE: 16

Met Asp Gln Pro Cys Cys Arg Ala Leu Tyr Asp Phe Glu Pro Glu Asn
1               5                   10                  15

Glu Gly Glu Leu Gly Phe Lys Glu Gly Asp Ile Ile Thr Leu Thr Asn
            20                  25                  30

Gln Ile Asp Glu Asn Trp Tyr Glu Gly Met Leu His Gly His Ser Gly
        35                  40                  45

Phe Phe Pro Ile Asn Tyr Val Glu Ile Leu Val Ala
    50                  55                  60

<210> SEQ ID NO 17
<211> LENGTH: 60
<212> TYPE: PRT
<213> ORGANISM: Artificial Sequence
<220> FEATURE:
<223> OTHER INFORMATION: SH3 285 - 344 aa

<400> SEQUENCE: 17

Met Asp Gln Pro Cys Cys Arg Gly Leu Tyr Asp Phe Glu Pro Glu Asn
1               5                   10                  15

Gln Gly Glu Leu Gly Phe Lys Glu Gly Asp Ile Ile Thr Leu Thr Asn
            20                  25                  30

Gln Ile Asp Glu Asn Trp Tyr Glu Gly Met Ile His Gly Glu Ser Gly
        35                  40                  45

Phe Phe Pro Ile Asn Tyr Val Glu Val Ile Val Pro
    50                  55                  60

<210> SEQ ID NO 18
<211> LENGTH: 61
<212> TYPE: PRT
<213> ORGANISM: Artificial Sequence
<220> FEATURE:
<223> OTHER INFORMATION: SH3 954 - 1014 aa

<400> SEQUENCE: 18

Pro Asn Leu Arg Thr Tyr Arg Ala Met Tyr Asp Tyr Ser Ala Gln Asp
1               5                   10                  15

Glu Asp Glu Val Ser Phe Arg Asp Gly Asp Tyr Ile Val Asn Val Gln
            20                  25                  30

Pro Ile Asp Asp Gly Trp Met Tyr Gly Thr Val Gln Arg Thr Gly Arg
        35                  40                  45

Thr Gly Met Leu Pro Ala Asn Tyr Ile Glu Phe Val Asn
    50                  55                  60

<210> SEQ ID NO 19
<211> LENGTH: 37
<212> TYPE: PRT
<213> ORGANISM: Artificial Sequence
<220> FEATURE:
<223> OTHER INFORMATION: WW 444 - 447 aa

<400> SEQUENCE: 19

Pro Ala Leu Pro Pro Gly Trp Glu Met Lys Tyr Thr Ser Glu Gly Val
1               5                   10                  15

Arg Tyr Phe Val Asp His Asn Thr Arg Thr Thr Thr Phe Lys Asp Pro
            20                  25                  30

Arg Pro Gly Ser Arg
        35
```

```
<210> SEQ ID NO 20
<211> LENGTH: 101
<212> TYPE: PRT
<213> ORGANISM: Artificial Sequence
<220> FEATURE:
<223> OTHER INFORMATION: SH2 14 - 102 aa

<400> SEQUENCE: 20

Trp Tyr Met Gly Pro Val Ser Arg Gln Glu Ala Gln Thr Arg Leu Gln
1               5                   10                  15

Gly Gln Arg His Gly Met Phe Leu Val Arg Asp Ser Ser Thr Cys Pro
            20                  25                  30

Gly Asp Tyr Val Leu Ser Val Ser Glu Asn Ser Arg Val Ser His Tyr
        35                  40                  45

Ile Ile Asn Ser Leu Pro Asn Arg Arg Phe Lys Ile Gly Asp Gln Glu
    50                  55                  60

Phe Asp His Leu Pro Ala Leu Leu Glu Phe Tyr Lys Ile His Tyr Leu
65                  70                  75                  80

Asp Thr Thr Thr Leu Ile Glu Pro Ala Pro Arg Tyr Pro Ser Pro Pro
                85                  90                  95

Met Gly Ser Val Ser
            100

<210> SEQ ID NO 21
<211> LENGTH: 90
<212> TYPE: PRT
<213> ORGANISM: Artificial Sequence
<220> FEATURE:
<223> OTHER INFORMATION: SH2 82 - 171 aa

<400> SEQUENCE: 21

Trp Phe His Gly Lys Ile Thr Arg Glu Gln Ala Glu Arg Leu Leu Tyr
1               5                   10                  15

Pro Pro Glu Thr Gly Leu Phe Leu Val Arg Gly Ser Thr Asn Tyr Pro
            20                  25                  30

Gly Asp Tyr Thr Leu Cys Val Ser Cys Asp Gly Lys Val Glu His Tyr
        35                  40                  45

Arg Ile Met Tyr His Ala Ser Lys Leu Ser Ile Asp Glu Glu Val Tyr
    50                  55                  60

Phe Glu Asn Leu Met Gln Leu Val Glu His Tyr Thr Ser Asp Ala Asp
65                  70                  75                  80

Gly Leu Cys Thr Arg Leu Ile Lys Pro Lys
                85                  90

<210> SEQ ID NO 22
<211> LENGTH: 97
<212> TYPE: PRT
<213> ORGANISM: Artificial Sequence
<220> FEATURE:
<223> OTHER INFORMATION: SH2 5 - 101 aa

<400> SEQUENCE: 22

Tyr Tyr His Gly Arg Leu Thr Lys Gln Asp Cys Glu Thr Leu Leu Leu
1               5                   10                  15

Lys Glu Gly Val Asp Gly Asn Phe Leu Leu Arg Asp Ser Glu Ser Ile
            20                  25                  30

Pro Gly Val Leu Cys Leu Cys Val Ser Phe Lys Asn Ile Val Tyr Thr
        35                  40                  45

Tyr Arg Ile Phe Arg Glu Lys His Gly Tyr Tyr Arg Ile Gln Thr Ala
    50                  55                  60
```

```
Glu Gly Ser Pro Lys Gln Val Phe Pro Ser Leu Lys Glu Leu Ile Ser
 65                  70                  75                  80

Lys Phe Glu Lys Pro Asn Gln Gly Met Val Val His Leu Leu Lys Pro
                 85                  90                  95

Ile

<210> SEQ ID NO 23
<211> LENGTH: 90
<212> TYPE: PRT
<213> ORGANISM: Artificial Sequence
<220> FEATURE:
<223> OTHER INFORMATION: SH2  460 - 549 aa

<400> SEQUENCE: 23

Trp Tyr His Gly Ala Ile Pro Arg Ala Glu Val Ala Glu Leu Leu Val
  1               5                  10                  15

His Ser Gly Asp Phe Leu Val Arg Glu Ser Gln Gly Lys Gln Glu Tyr
                 20                  25                  30

Val Leu Ser Val Leu Trp Asp Gly Leu Pro Arg His Phe Ile Ile Gln
             35                  40                  45

Ser Leu Asp Asn Leu Tyr Arg Leu Glu Gly Glu Gly Phe Pro Ser Ile
         50                  55                  60

Pro Leu Leu Ile Asp His Leu Leu Ser Thr Gln Gln Pro Leu Thr Lys
 65                  70                  75                  80

Lys Ser Gly Val Val Leu His Arg Ala Val
                 85                  90

<210> SEQ ID NO 24
<211> LENGTH: 98
<212> TYPE: PRT
<213> ORGANISM: Artificial Sequence
<220> FEATURE:
<223> OTHER INFORMATION: SH2 144 - 241 aa

<400> SEQUENCE: 24

Trp Tyr Phe Gly Lys Ile Gly Arg Lys Asp Ala Glu Arg Gln Leu Leu
  1               5                  10                  15

Ser Pro Gly Asn Pro Gln Gly Ala Phe Leu Ile Arg Glu Ser Glu Thr
                 20                  25                  30

Thr Lys Gly Ala Tyr Ser Leu Ser Ile Arg Asp Trp Asp Gln Thr Arg
             35                  40                  45

Gly Asp His Val Lys His Tyr Lys Ile Arg Lys Leu Asp Met Gly Gly
         50                  55                  60

Tyr Tyr Ile Thr Thr Arg Val Gln Phe Asn Ser Val Gln Glu Leu Val
 65                  70                  75                  80

Gln His Tyr Met Glu Val Asn Asp Gly Leu Cys Asn Leu Leu Ile Ala
                 85                  90                  95

Pro Cys

<210> SEQ ID NO 25
<211> LENGTH: 97
<212> TYPE: PRT
<213> ORGANISM: Artificial Sequence
<220> FEATURE:
<223> OTHER INFORMATION: SH2 439 - 535

<400> SEQUENCE: 25

Trp Phe His His Lys Ile Ser Arg Asp Glu Ala Gln Arg Leu Ile Ile
  1               5                  10                  15
```

```
                                     -continued

Gln Gln Gly Leu Val Asp Gly Val Phe Leu Val Arg Asp Ser Gln Ser
                20              25              30

Asn Pro Lys Thr Phe Val Leu Ser Met Ser His Gly Gln Lys Ile Lys
            35              40              45

His Phe Gln Ile Ile Pro Val Glu Asp Gly Glu Met Phe His Thr
 50                  55                  60

Leu Asp Asp Gly His Thr Arg Phe Thr Asp Leu Ile Gln Leu Val Glu
 65              70              75                          80

Phe Tyr Gln Leu Asn Lys Gly Val Leu Pro Cys Lys Leu Lys His Tyr
                85              90                      95

Cys
```

US 8,541,166 B1

PEPTIDE SEQUENCES FOR BINDING INFECTIOUS PRIONS

RELATED APPLICATIONS

This application claims priority to U.S. Provisional Patent Application Ser. No. 61/101,447, filed Sep. 30, 2008 the contents of which are incorporated herein by reference in their entirety.

FIELD OF THE INVENTION

The present invention relates to novel peptide sequences that specifically bind infectious prion protein.

BACKGROUND OF THE INVENTION

Transmissible spongiform encephalopathies are incurable, fatal neurodegenerative diseases characterized by the accumulation of abnormal prion protein (PrPsc), neuronal cell death and vacuolation of brain tissue (1). The PrPsc protein is extractable from diseased tissue and is distinguished from endogenous PrPc by partial protease resistance and detergent insolubility (2). The transmissible agent is the PrPsc protein and it serves as a template for the molecular conversion of endogenous host PrPc into the abnormal PrPsc structural isoform (3, 4). Host expression of PrPc is necessary for disease transmission, as ablation of the PrPc gene prevents disease (5) whereas the over expression of PrPc followed by PrPsc challenge accelerates disease (6, 7). The molecular events that mediate neuronal PrPc to PrPsc conversion, not simply accumulated PrPsc, appears to be the initiating factor mitigating the neurodegenerative disease process (8, 9). Bovine Spongiform Encephalopathy (BSE) is one example of many prion diseases that include Scrapie in sheep and goats, chronic wasting disease (CWD) in deer and elk, and Kuru and Creutzfeldt-Jakob disease (CJD) in humans. Prions are thought to propagate in infected hosts by a novel mechanism that occurs when normal prion protein (PrPc) becomes "misfolded" into an abnormal infectious form (PrPsc), in a template-driven process. Unlike conventional microbes, prions do not require an agent-specific nucleic acid in order to multiply. The protein nature of prions makes them difficult to detect and nearly impossible to treat and control.

Current technologies inadequately address the inherent problems in prevention of PrPsc transmission, early detection and decontamination from animals and environmental by-products. Fundamentally, these issues reflect the fact that both PrPc and PrPsc have identical primary structures, differing in three-dimensional configuration only. To date no unique antibodies or surrogate markers have been identified that can distinguish between PrPc and PrPsc. This has created an extremely difficult and challenging dilemma in regard to the detection, vaccination and treatment of PrPsc (5).

Definitive diagnosis of PrPsc in animals requires assessment of clinical symptoms and post-mortem evaluation of brain tissue for spongiform degeneration. Pre-clinical assessment of animal status via non-invasive sampling has proven difficult and unreliable. The most definitive method to confirm the presence of infectious PrPsc requires an arduous animal bioassay. Biochemical assays all utilize a complex sequence of steps applied to tissue samples that exploit the resistance of PrPsc, relative to PrPc, to enzymatic degradation by Proteinase K (PK). Confirmation of PrPsc is defined by the detection of remaining PK resistance protein by a PrPc antibody (5-6). These methods detect only PK-resistant PrPsc, are prone to variability, and are inadequate for detection of low level PrPsc in contaminated samples such as blood.

SUMMARY OF THE INVENTION

Method of identifying peptides that specifically interact with intact prion isoforms (PrPsc) or native PrPc proteins is disclosed herein.

Identification of protein and peptide sequences that specifically bind to PrPsc, PrPc or both are also disclosed herein.

Methods of detecting prions in potentially infected animal and environmental samples are also disclosed.

Methods for diagnostic detection of prion diseases in biological samples using identified protein and peptides markers as surrogate analytes.

Methods for therapeutic intervention in prion diseases using identified protein and peptides as biological targets for pharmaceutical drugs, immunomodulation, and other chemical agents.

Methods for the development of novel drugs or reagents that modulate identified protein and peptide targets for the detection and treatment of prion diseases.

Methods for the capture, isolation, enrichment and inactivation of prions from biological and environmental samples.

BRIEF DESCRIPTION OF THE DRAWINGS

FIG. 1. is a picture of the isolation and enrichment of prion in detergent resistant membranes (drm) from hamster brain homogenate.

Figure 2:
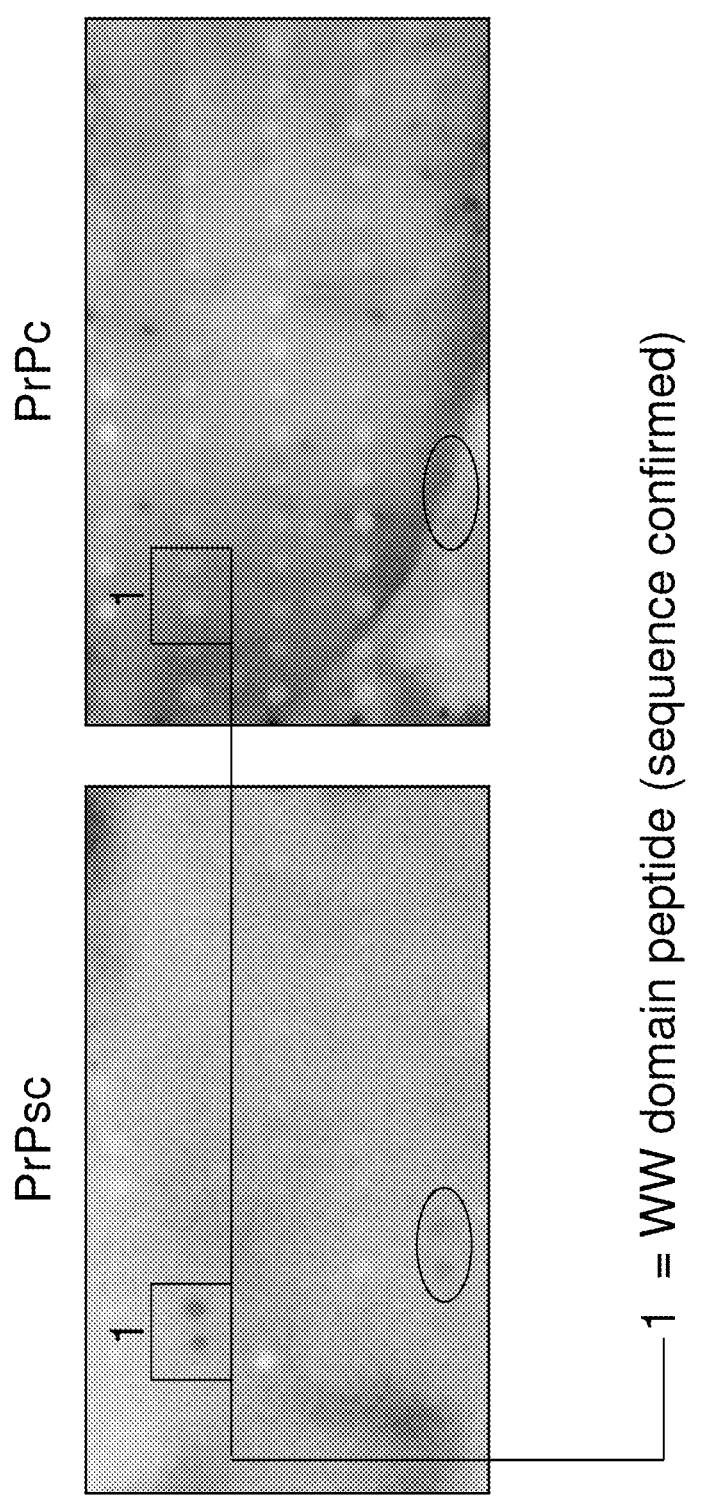

FIG. 2 is a photo of specific prion binding to WW domain peptide.

FIG. 3 is a photo of specific prion binding to PDZ peptides.

FIG. 4 is a photo of specific prion binding to PDZ peptides.

FIG. 5 is a photo of specific prion binding to SH3 peptides.

FIG. 6 is a photo of specific prion binding to SH3 peptides.

FIG. 7 is a photo of specific prion binding to SH2 peptides.

FIG. 8 is a diagram of the assay strategies for detection of infectious prions using selective binding to synthetic peptides of the invention.

DETAILED DESCRIPTION OF THE INVENTION

The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement.

Herein is described a novel approach to identify peptides that specifically interact with intact PrPsc or PrPc protein isoforms.

We isolated both PrPc and PrPsc biochemically within detergent resistant membranes (DRMs) (FIG. 1), used this material to probe peptide libraries that correspond to defined functional domains of whole proteins, and identified novel peptides that bind specifically to PrPsc and PrPc (FIGS. 2-7). The peptides spotted in these arrays correspond to the specific functional domains of known proteins. These families of functional domains mediate protein-protein interaction within cells and are involved in intracellular trafficking and signal transduction. Importantly, the binding specificity observed in our data likely reflects the three-dimensional conformational differences between PrPsc and PrPc. Moreover, the conformational endpoint of a specific 'strain' of infectious prion would likely show a distinct peptide-binding fingerprint useful in identification.

An embodiment is unique peptide sequences that specifically bind to PrPc, PrPsc or both using peptide arrays on PVDF membranes.

Another embodiment of the invention is the use of unique peptide sequences as arrays that specifically bind PrPsc and isoforms thereof in detection assays of potentially infected animal and environmental samples.

Peptides with selective binding for PrPsc, PrPc or both would be used to develop a sample evaluation array allowing for rapid detection of infectious PrPsc and strain identification. Variations of these arrays can be employed as: 1) spots on PVDF membrane, 2) peptide bound ELISA plates, 3) affinity columns, and 4) labeled molecular probes (FIG. 8). Peptide affinity columns could be used to enrich for PrPsc from low level samples such as body fluids. Direct labeled peptide probes could be used in concert with prion antibodies to identify PrPsc.

These assays may be independent or combined with current methodologies used for the detection of infectious prions. Moreover, utilization of specific qualitative binding differences would allow for capture and enrichment of PrPsc from samples (i.e. body fluids) from pre-clinical animals with low-level contaminant (5-50 fmol) below current assay detection limits.

Method of identifying peptides that specifically interact with intact prion isoforms (PrPsc) or native PrPc proteins is disclosed herein. PrPc derived sequences are available in bacterial and mammalian cell expression vectors and recombinant protein can be produced and purified resulting in source of PrPc protein and peptide for interaction. As PrPsc is a conformational isoform of PrPc and cannot be produced by recombinant technology. Some work to produce isoforms of PrPsc in vitro have been demonstrated { }. Here we outlined a methodology to enrich and purify both PrPc and PrPsc from tissue. This method uses the detergent resistant properties of PrPsc and its association with specialized membrane microdomains. Disruption of tissue in detergent at 4 C is followed by high speed centrifugation in a discontinuous sucrose gradient 5-40%; a process that allows for the isolation of PrPc and PrPsc with detergent resistant membranes (DRMs). This method allows for the enrichment of both native PrPc and infectious PrPsc effectively removing >99.75% of contaminating proteins. PrPc, but not PrPsc, can be proteolytically digested in DRMs by addition of proteinase-K (15 ug/ml 1 h at 60 C) with only PK-resistant PrPsc remaining in the sample. The interaction of peptide or protein domains with either PrPc, PrPsc or both can be determined by differential comparison. Briefly, DRMs from normal tissue containing only PrPc, DRMs from infected tissue digested with PK containing only PrPsc are incubated with protein or peptide sequences (ie. attached to membranes or microwell plates) allowed to interact then probed with antibodies against the PrP protein and positive interactions determined (ie. horseradish peroxidase [HRP] conjugated antibodies followed by chemiluminescent detection [ECL]). Comparative analysis of positive interactions would allow for the identification of specific prion interactions (ie. PrPc negative but PrPsc positive).

Identification of protein and peptide sequences that specifically bind to PrPsc, PrPc or both are also disclosed herein. Using the methodology describe above, recombinant peptides corresponding to known functional domains spotted on PVDF membranes (Panomics) and specific interactions determined. The following sequences were identified:

Methods of detecting prions in potentially infected animal and environmental samples are also disclosed. Prion specific peptides can be readily adapted to current protein detection strategies. These sequences can be directly or indirectly labeled (enzymatic or dyes) and used as diagnostic probes functioning in a manner similar that of an antibody. Prion specific sequences could be attached to a micro-well plate to capture prion from biological or environmental samples and then probed with prion specific reagents (peptides or antibodies) for detection.

Methods for diagnostic detection of prion diseases in environmental or biological samples using identified protein and peptides markers as surrogate analytes. Prion specific proteins and peptides may be either physiological or non-physiological. Physiological prion specific protein interactions maybe used as surrogate biomarkers for the detection of prions. For example a complex formed between specifically between a prion and unique peptides may allow the peptide to serve as a surrogate biomarker for the indirect detection of prions via antibody based detection of the surrogate peptide. If the peptide sequence in not physiological (ie not found in the sample) it could be added to either a biological or environmental sample, allowed to interact with prion, then detected with an antibody that binds to the peptide sequence. Antibodies against prion specific peptides in conjunction with antibodies against the prion protein could be combined with current detection methods (ELISA) to provide a multi-labeled detection strategy. Prion and PrPc specific peptides could be added in proprietary multi-valent combinations along with corresponding antibodies for detection prion isoforms. Direct labeling of prion specific peptides or indirect targeting using surrogate reagents (ie antibodies) could be used for clinical detection of prion disease by imaging.

Methods for therapeutic intervention in prion diseases using identified protein and peptides as biological targets for pharmaceutical drugs, immunomodulation, and other chemical agents. Physiological proteins or peptides that specifically interact with prion could be direct targets of pharmaceutical drugs. Disruption of the physiological interaction of prions or PrPc with associated proteins or peptides may be used to disrupt, cure or alter prion diseases. Protein or peptides sequences specific for PrPc or Prion may be modified as to serve as targeted carrier of therapeutic drugsor chemical agents (quiocrine, amphotericin D, beta-sheet breakers or death domains) that disrupt, destroy or impede the propagation of prions in those inflicted or exposed to prions. Vaccination or antibody production against prion specific peptide and prion-peptide complex maybe used to generate a therapeutic immune response for treatment or cure of disease.

Methods for the development of novel drugs or reagents that modulate identified protein and peptide targets for the detection and treatment of prion diseases. Prion specific peptide complexes may serve as molecular targets for the generation of specific antibodies. These antibodies may then be used alone or with the addition of peptide to biological or environmental samples for the detection of prions. Antibodies generated against specific prion-peptide complexes may be used as reagents for diagnosis of disease and detection of prion in biological and environmental samples. Specific physiological prion-peptide complexes associated with disease may be used as targets for the development of therapeutic drugs.

Methods for the capture, isolation, enrichment and inactivation of prions from biological and environmental samples. Prion specific sequences may be used in the capture and enrichment of prion from biological or environmental samples. These peptides maybe covalently attached to a matrix (filter) and samples applied in small or large volumes to deplete prion from sample. Moreover this approach can be used to enrich prions from samples for detection following elution. Prion specific peptides may be bound as spots to membranes (PVDF or Nitrocellulose) or attached to microwell plates to generate an array of protein interactors capable of distinguishing prion isoforms by distinct pattern of interactions from biological and environmental samples. Specific peptide sequences may bind and inactivate the conformational conversion of PrPc to PrPsc effectively inactivating prions. These peptides may be used directly or with modification for direct treatment of prion diseases.

What is claimed:

1. A method for the capture, isolation, or detection of prions from animal or environmental samples, said method comprising:

contacting a potentially infected animal or environmental sample with the prion specific peptide comprising SEQ ID NO:1;

and detecting the specific binding of prions from the sample to the prion specific peptide comprising SEQ ID NO:1.

* * * * *